United States Patent [19]

Cohen

[11] Patent Number: 4,764,632

[45] Date of Patent: Aug. 16, 1988

[54] MULTIFUNCTIONAL AMINO ZIRCONIUM ALUMINUM METALLO ORGANIC COMPLEXES USEFUL AS ADHESION PROMOTER

[75] Inventor: Lawrence B. Cohen, Sharon, Mass.

[73] Assignee: Cavedon Chemical Company, Inc., Woonsocket, R.I.

[21] Appl. No.: 816,814

[22] Filed: Jan. 7, 1986

[51] Int. Cl.⁴ ............................ C07F 5/06; C07F 7/00
[52] U.S. Cl. ................................. 556/27; 544/4; 544/181; 544/225; 546/2; 546/5; 546/6; 548/101; 548/104; 548/105; 548/109; 548/402; 548/403
[58] Field of Search ............... 556/27; 548/105, 403; 548/109, 402

[56] References Cited

U.S. PATENT DOCUMENTS

| | | | |
|---|---|---|---|
| 2,832,754 | 4/1958 | Jex et al. | 260/46.5 |
| 2,930,809 | 3/1960 | Jex et al. | 260/448.8 |
| 2,941,918 | 6/1960 | West | 154/140 |
| 2,946,701 | 7/1960 | Plueddemann | 117/72 |
| 3,030,320 | 4/1962 | Haslam | 260/18 |
| 3,032,570 | 5/1962 | Haslam | 260/429.5 |
| 3,044,982 | 7/1962 | Jex et al. | 260/46.5 |
| 3,045,036 | 7/1962 | Jex et al. | 260/448.8 |
| 3,334,119 | 8/1967 | Cohen | 260/429 |
| 3,405,153 | 10/1968 | Jones et al. | 260/429.3 |
| 3,419,587 | 12/1968 | Harson | 260/429.3 |
| 3,553,316 | 1/1971 | Rubino | 260/429.3 |
| 3,660,134 | 5/1972 | Morris et al. | 106/308 |
| 3,697,474 | 10/1972 | Morris et al. | 260/41 A |
| 3,792,068 | 2/1974 | Luedders et al. | 260/429.3 |
| 3,981,986 | 9/1976 | Rubino | 260/429.3 |
| 4,017,599 | 4/1977 | Rubino | 260/429.3 X |
| 4,080,353 | 3/1978 | Monte et al. | 260/429.3 X |
| 4,102,642 | 7/1978 | Banks | 8/125 |
| 4,141,751 | 2/1979 | Moreland | 106/308 |
| 4,152,311 | 5/1979 | Monte et al. | 260/29.2 EP |
| 4,223,010 | 9/1980 | Rubino et al. | 424/66 |
| 4,360,544 | 11/1982 | Franz et al. | 428/432 X |
| 4,414,275 | 11/1983 | Woods | 428/411 X |
| 4,539,048 | 9/1985 | Cohen | 106/287.17 |
| 4,539,049 | 9/1985 | Cohen | 106/287.17 |

Primary Examiner—H. M. S. Sneed
Assistant Examiner—George R. Fourson
Attorney, Agent, or Firm—Ernest V. Linek; David G. Conlin

[57] ABSTRACT

This invention relates to novel compositions of matter which are multifunctional amino zirconium aluminum metallo organic complexes which are comprised of a chemically united complex aluminum moiety, a tetravalent zirconium moiety, and a multifunctional amino acid wherein the acid is chemically bound to both the aluminum and zirconium centers.

Such compositions are useful in promoting adhesion of adhesives, sealants, and coatings to metal, rubber, glass, plastic, coatings, and wood thereby enhancing strength properties and prolonging useful service life when such products are exposed to aggressive environments.

Futher described is the specific process for the preparing of such compositions in organic media with desirable stability of the metal centers toward polymerization and related hydrolysis.

21 Claims, 3 Drawing Sheets

MULTIFUNCTIONAL AMINO ZIRCONIUM ALUMINUM METALLO ORGANIC COMPLEXES USEFUL AS ADHESION PROMOTER

BACKGROUND OF THE INVENTION

This invention relates to compositions which are useful for enhancing adhesion of adhesives, sealants, and coatings to various substrates including metals such as aluminum and steel, rubber, glass, plastics, and wood or combinations thereof. The adhesive bond formed to the substrate must be able to maintain its integrity upon exposure to aggressive environments such as exposure to heat, moisture, salt spray, solvents, and acids. In the specific instance of adhesives, stresses which are placed upon the bonded assembly must not be allowed to cause adhesive failure.

Adhesives, sealants, and coatings are closely related products all requiring excellent adhesion. Most fundamentally, an adhesive is used to bond two surfaces together so that the assembly may withstand stress, a sealant is used to cover a boundary where two or more materials meet, and a coating is used to both protect a single type of material from the deleterious effects of the environment and also to enhance surface aesthetics.

It is recognized by those skilled in the art that such adhesives may include epoxys, phenolics, and various elastomeric resins such as nitrile, neoprene, vinyl butyural, SBR, EPDM, polyurethane, silicone, and styrene butadiene block copolymers.

Sealants are compositionally related to adhesives and may include polyurethanes, polyvinyl chloride plastisols, vinyl, nitrile, EPDM, silicone, neoprene, SBR, styrene/butadiene block copolymers, and water based systems such as SBR, acrylic or polyvinyl acetate. The sealant is actually a thick coating which must additionally be able to respond to stresses placed upon the joined components without rupture; hence, unlike coatings they are generally elastomeric.

High performance coatings are formulated primarily to protect surfaces against aggressive environmental agents. Of the three classes of materials, coatings is unique in having little concern regarding withstanding stresses. Hence, coating resins encompass a different set of resins including alkyds, acrylic, epoxy, epoxyester, saturated polyester/melamine, unsaturated polyester, polyurethane, silicones, vinyl, and vinyl toluene.

Sealant and adhesive manufacturers have historically used silanes to enhance adhesion. The usefulness of silanes is in part mitigated by their high cost, difficulty in handling owing to water sensitivity, and the limiting specificity of silane containing adhesives and sealants for certain substrate types, i.e., glass rubber, and only marginally metals.

The compositions described herein are related to aluminum zirconium metallo organic complexes described in U.S. Pat. Nos. 4,539,048 and 4,539,049. Unlike the predecessor complexes, the subject compositions have multiple organofunctional groups in each molecule which contains a minimum of one amine group. Such compositions may not be synthesized in accordance with the teachings of the prior art due to the high reactivity of the organofunctional groups which induce inorganic polymerization; hence, the multifunctional amino zirconium aluminum complexes of the present invention may only be synthesized utilizing the process technology described herein, i.e., in a solvent which is capable of chelating with the metals and thus prevents the polymerization of the Al and Zr species.

SUMMARY OF THE INVENTION

The present invention is directed to a composition of matter comprising the reaction product of a chelated aluminum moiety, an organofunctional ligand, and a zirconium oxyhalide, the organofunctional ligand being complexed with and chemically bound to the chelated aluminum moiety and the zirconium moiety, the aluminum moiety having the formula:

wherein A or B is hydroxy or halogen and a, b, and c are numerical values such that $2a+b+c=6$, and $(OR_1O)$ is an alpha, beta or alpha, gamma glycol group in which $R_1$ is an alkyl group having 1 to 6 carbon atoms; the organofunctional ligand is a multifunctional amino acid residue having the formula:

wherein $R_2$ is (1) an alkyl, aryl, or aralkyl group having from 1 to 8 carbon atoms, or (2) a bicyclic N-heterocyclic aryl group having from 7 to 11 carbon atoms; Y' is an amino, hydroxy, carboxy, mercapto, methylmercapto, or sulfide group, and wherein the amine group(s) may be bound to primary or secondary carbon atoms; and the zirconium oxyhalide moiety which may be used as either an aqueous solution or dry powder has the formula:

wherein A, B are as above defined and $d+e$ are numerical values such that $d+e=4$; the ratio of chelated aluminum moiety to zirconium oxyhalide moiety being from about 1.5 to 10.0, and the molar ratio of organofunctional ligand to metal being from about 0.05 to 2.

These compositions are useful in promoting adhesion of adhesives, sealants, and coatings to metal, rubber, glass, plastic, coatings, and wood thereby enhancing strength properties and prolonging useful service life when such products are exposed to aggressive environments.

DETAILED DESCRIPTION OF THE PREFERRED EMBODIMENTS

The subject invention pertains to compositions of matter which are the complex reaction products of (I) chelate stabilized aluminum compositions (preferably chelate stabilized aluminum chlorohydrates), (II) zirconium oxyhalide (preferably oxychloride), and (III) multifunctional amino carboxylic acid(s). The reactants utilized to obtain the compositions of the present invention can generally be represented by the empirical formulae (I), (II), and (III):

wherein: A and B may be halogen, most preferably chlorine, or hydroxy. Preferably A and B are chloro or hydroxy; a is a numerical value ranging from about 0.05 to 2, preferably 0.1 to 1; b is a number ranging from about 0.05 to 5.5, preferably about 1 to 5; and c is a number ranging from 0.05 to 5.5, preferably about 1 to 5, provided that $2a+b+c=6$ in the chelate stabilized aluminum reactant. Most preferably A is hydroxy and b ranges from 2 to 5, and B is chlorine and c ranges from 1 to 3.8. The variables d and e have a numerical value from 0.05 to 4, provided that $d+e=4$ in the zirconium oxyhalide metallo organic complex reactant. Preferably there is at least one hydroxy group and one halogen group in the zirconium reactant. More preferably the empirical ratio of hydroxy to the zirconium in this group is from about 1-2, and the ratio of halogen to zirconium is about 2-3, in that reactant.

In the aluminum containing segment of Formula I, pairs of aluminum atoms are joined by bidentate chelating ligand wherein:

(1) —$OR_1O$— is an alpha, beta or alpha, gamma glycol group in which $R_1$ is an alkyl group having from 1 to 6 carbon atoms, preferably having 2 or 3 carbon atoms.

In each instance the organic ligand is bound to two aluminum atoms through two oxygen heteroatoms.

The organofunctional ligand, —$OC[R_2(Y')NH_2]O$— is a moiety which can be derived from one of the following groups:

(1) An amino acid wherein $R_2$ is an alkyl, aryl, or aralkyl group having from 1 to 8 carbon atoms, wherein Y' is an amino, hydroxy, carboxy, mercapto, methyl mercapto, or sulfide group, and wherein the amino group(s) may be bound to primary or secondary carbon atoms.

(2) An amino acid wherein $R_2$ is a bicyclic (N-heterocyclic aryl) group having from 7 to 11 carbon atoms, the heterocycle containing saturated or unsaturated carbon atoms, wherein Y' is an amino, hydroxy, carboxy, mercapto, methyl mercapto, or sulfide group, and wherein the amine group(s) may be bound to primary or secondary carbon atoms.

An extensive variety of —$OC[R_2(Y')NH_2]O$— anionic ligands are useful in the preparation of the subject compositions. Examples of specific amino acids include anions of: glycine, alanine, valine, leucine, isoleucine, phenylalanine, tyrosine, tryptophan, serine, threonine, methionine, cysteine, cystine, proline, hydroxyproline, aspartic, glutamic, lysine, arginine, and histidine.

While not wishing to be bound by theory, characterization of said compositions using infrared spectroscopy (e.g. FIGS. 1 to 6) has indicated that generally greater than 90% of the organofunctional ligand, $OC[R_2(Y')NH_2]O$— is present in complex form (i.e. has reacted) in the aluminum zirconium metallo organic and furthermore, that the organofunctional ligands are bound to an aluminium metal center on the one hand and to a zirconium metal center on the other. The IR information also has indicated that the chelating agent (—$OR_1O$—) forms a chelated complex with aluminum.

Thus the reaction product apparently involves the chelated aluminum moiety bridged to the zirconium oxychloride moiety through the organofunctional ligand. This may be empirically represented by Formula (IV):

wherein A and B are as above-defined, and a, b, c, d and e are as above defined, except that, in order to form the bonds depicted, the substituents attached to the metal groups are appropriately reduced, i.e. $2a+b+c=4$ ($2a+b+c=5$ when the aluminum moiety is a terminal group), and $d+e=2$ ($d+e=3$ when zirconium moiety is a terminal group). When the aluminum moiety or the zirconium moiety forms the terminus in the molecular chain, one of the A or B groups may be replaced by a lower glycoxy or alkoxy (if available) group having 1 to 6 carbon atoms.

X, Y and Z are at least each 1, and may vary from 1 to 100 or more, depending on the reactivity of the particular materials and the desired form of the product. The molar ratio of aluminum moiety to zirconium moiety (X to Z) may vary from about 1.0 to 10, with the preferred ratio being from about 1.5 to 5. The ratio of organofunctional ligand to total metal (Y/(2X+Z)) may vary from about 0.05 to 2.0, with the preferred ratio being about 0.1 to 1.0.

The composition of the present invention is preferably not prepared in a solvent such as those disclosed in U.S. Pat. Nos. 4,359,048 and 4,359,049, in order to avoid encountering undesirable hydrolysis and polymerization reactions which can result in a highly polymeric solid reaction product. Preferred solvents for use in this invention substantially prevent such polymerization.

Preparation of the subject composition is most preferably attained in a solvent consisting of alkyl glycols (or polymers thereof) having from 1 to 6 carbon atoms (in each repeating unit) and water; or alkyl glycols having from 1 to 6 carbon atoms, and water or lower alcohol having from 1 to 3 carbon atoms, wherein the water or lower alcohol content in each instance may be about 0.1 and must not exceed 10%. Preferably the solvent mixture contains a plurality of alkyl glycols, preferably propylene glycol, in an amount of from about 93% to 100%. The active matter of compositions as prepared in such solvents is from about 10% to 70%, preferably from about 15% to 60%. Pursuant to such preparation, the product may be spray dried or otherwise solvent stripped to leave a solid having high activity.

The present invention also provides a process for preparing compositions described above. Hydrolytically stable products having a shelf life in excess of 30 days can be prepared by complexation of a dimeric aluminum chlorohydrate moiety with a bidentate chelating ligand which imparts hydrolytic stability, such as alpha,beta or alpha, gamma glycol, having from 1 to 6 carbon atoms, the preferred ligands having from 2 to 3 carbon atoms. Such complexation should utilize a mole ratio of complexing ligand to Al of about 0.05 to 2, the preferred ratio being about 0.10 to 1.00. The stabilized aluminum complex can be prepared as either an isolated composition prior to introduction of the zirconium moiety or prepared in situ with zirconium oxychloride, the preferred route being preparation of the stabilized aluminum complex as a separate, isolated composition. Preferably the dimeric aluminum reactant is dissolved in propylene glycol and the mixture heated at from about 65° to 70° C. for one hour to form the stabilized dimeric aluminum complex.

The process for successful complexation with $OC(R_2(Y')NH_2)O$, the organofunctional ligand, varies as a function of the physical form of the zirconium oxychloride used. When zirconium oxychloride solution (aqueous) is used the organofunctional ligand is most preferably added to a glycol solution of zirconium oxychloride and thereafter the stabilized aluminum chlorohydrate is fed into this mix with heating. When zirconium oxychloride (solid) is used the organofunctional ligand may be added only after the formation of a solution comprised of zirconium oxychloride (solid) in a large quantity of glycol and a lesser amount of lower alcohol having from 1 to 3 carbon atoms or water. The latter reaction should include from about 0.1 to 10.0 percent lower alcohol or water, most preferably from about 2 to 6 percent. For each procedure, the reaction should employ a mole ratio of $OC[R_2(Y')NH_2]O$ to total metal of between about 0.05 and 2, the most preferred ratio being about 0.1 to 1.0. The route elected for synthesis will result in a significant difference in end product composition as characterized by performance in various applications of said compositions. Preferably the organofunctional ligand is admixed with zirconium oxychloride in propylene glycol and heated at about 70° C. for 0.5 hours; whereupon a propylene glycol solution of the stabilized dimeric aluminum complex is fed to the mixture over from about 0.15–0.50 hours. The reaction is completed by further heating at about 70° C. for 0.5 hours.

Compositions prepared in accordance with the teachings of the subject invention are characterized as clear and colorless having a viscosity of from about 100–200 cps and a shelf life in excess of one year.

While not wishing to be bound by theory, the products of this present invention have a multiplicity of highly reactive organic groups which are postulated to catalyze the rapid polymerization of the aluminum and zirconium centers by facilitating extended inorganic polymer formation resulting from hydroxy and oxo groups bridging such centers. The elimination of such undesirable extended polymer formation is postulated to occur as a result of preferential complexation with the bulk glycol phase which is present in substantial stoichiometric excess. It is thus concluded that the subject compositions of the present invention, multifunctional amino zirconium aluminum metallo organic complexes, are unable to be synthesized in other than glycolic media.

The utility of these compositions is manifested most dramatically when used in adhesive formulations, such formulations exemplified by resin components which may include, but are not limited to epoxy, phenolic, and various elastomers such as nitrile, vinyl butyral, SBR, EPDM, polyurethane, silicone, neoprene, styrene/butadiene block copolymers, and the like when applied to various substrates including metal, rubber, plastic, glass, and wood. Addition of the adhesion promoter may be made to the resin, solvent, or finished adhesive formulation at a level of from about 0.05 to 10.00 weight percent of the contained resin solids, most preferably from about 0.25 to 3.00 percent of the contained resin solids. It is recognized that such adhesion promoters will furthermore have an affinity for contained pigment or mineral/filler and that where such substances are present the optimum use level of the adhesion promoter must be increased to provide sufficient quantity to modify such particulate surfaces while maintaining an unreacted residual quantity to function as an adhesion promoter.

While not wishing to be bound by theory it is postulated that the high surface energies characteristic of such adhesion promoters thermodynamically contributes to their tendency to leave the low surface energy resin of the adhesive, coating or sealant and hence, collect at interfaces where the pendant hydroxy groups attached to the aluminum and zirconium centers are postulated to form covalent and hydrogen bonds in the specific instance of adhesive use on metal, glass, wood, and polar rubber and plastic surfaces. The multiple organofunctional groups of the adhesion promoter thereupon form covalent bonds to reactive sites in the adhesive resin upon drying or curing. In the absence of reactive sites in the adhesive resin for example EPDM, butyral rubbers it is postulated in accordance with accepted theory that interpenetration into the bulk resin phase occurs by the organofunctional portion of the adhesion promoter. This explanation of what is termed "basic adhesion" (K. L. Mittal) is responsible for sizable increases in "practical adhesion" by which is meant measurable macroscopic improvement in strength properties of the bonded adherents.

In similar fashion, the subject adhesion promoters are useful compositions for promoting the adhesion of coatings to metals most specifically, and to rubber, wood, glass, plastics, and other coatings more generally. Such coatings are comprised of resins which may include, but are not limited to alkyd, acrylic, epoxy, epoxyester, phenolic, saturated polyester/melamine, unsaturated polyester, polyurethane, silicone, vinyl, and vinyl toluene. The subject adhesion promoters find use in conventional coatings (i.e., solids less than about 75 weight percent), high solids coatings (i.e., solids greater than about 75 weight percent), and water-borne coatings. The solubility of the adhesion promoter is sufficient so that it may be added to all commonly encountered coating solvents which may include, but are not limited to, mineral spirits, toluene, xylene, ketones, alcohols, glycols, glycol ethers, tetrahydrofuran, oils, halogenated hydrocarbons, and water. Alternatively, the adhesion promoter may be added directly to the aforementioned resins. Irrespective of the mode of addition, solubility and hence performance, are optimized by use of a high shear mixer, for example Cowles ® type.

In the coatings industry it is most common to describe use level as a function of pigment content, therefore, it is recommended that from about 0.10 to 10.00 phf (parts per hundred filler or pigment) is added, the preferred ratio being from about 0.50 to 2.00 phf. The adhesion promoter when used in the grind phase (prior to pigment addition) will function additionally as a pigment dispersant and viscosity depressant. Usage level must allow for pigment surface modification and subsequently a residual unreacted quantity for adhesion promotion. The theory describing the molecular behavior responsible for improved adhesion is as already described. The use of such adhesion promoters in coatings will most generally result in a sharp reduction in corrosion when applied to metal surfaces as a result of the agents of corrosion, water and oxygen, being unable to penetrate to the coating metal interface. The reduction in corrosion will be generally quantified as an increase in the number of hours of salt spray or humidity exposure prior to failure. Adhesive strengths may also be measured.

Coatings using multifunctional amino zirconium aluminum metallo organic complexes are not restricted to use solely on metallic substrates. Such compositions are also useful in promoting intercoat adhesion whereby a second coat is applied to a primer or base coat which may or may not have been dried or cured. In like fashion since the base coat forms a plastic surface improved adhesion of coatings to plastics may also be observed.

In pigment free coatings generally referred to as clear coats and most often comprised of acrylics or urethanes, the adhesion promoter may be added to the resin at a level of from about 0.10 to 10.00 weight percent of resin solids, the preferred ratio being from about 0.25 to 2.00 phf. It is a further object of this invention to provide adhesion promoters containing not more than about 3 weight percent water which will be useful in systems wherein water cannot be tolerated as exemplified by most urethanes.

The subject adhesion promoters are lastly useful in promoting adhesion of sealant formulations, such formulations exemplified by resin components which may include, but are not limited to polyurethanes, polyvinyl chloride plasisols, vinyl, nitrile, EPDM, silicone, neoprene, SBR, styrene/butadiene block copolymers thereof when applied to various substrates including metal, rubber, plastic, glass and wood. Sealants may generally be viewed as thick coatings (>50 mils) which are applied at the boundary between two or more materials which are most often dissimilar materials. Hence, the sealant must possess excellent adhesion to all materials constituting that boundary. Use levels for the subject compositions will vary from about 0.10 to 10.00 weight percent of resin solids, the preferred ratio being from about 0.25 to 2.00 weight percent. When such sealant compositions are pigmented or contain mineral fillers, it is recommended that from about 0.10 to 10.00 phf is added, the preferred ratio being from about 0.50 to 2.00 phf. Improvements in other sealant properties such as elongation and sag may also be realized.

EXAMPLE 1

Preparation of Sec-Propanolato Aluminum Chlorhydrate Solid

Aluminum chlorhydrate, 0.197 moles Al (21.38 g, 5/6 basic) is dissolved in an equal part of water. The solution is brought to reflux, whereupon a methanolic solution of propylene glycol, 0.0985 moles (7.49 g), is fed to the reactor and reflux maintained subsequent to the addition for ½ hour. The reaction product solution is placed in a drying oven at 100° C. to 120° C. for one hour to remove solvent. The dried powder remaining is sec-propanolato aluminum chlorhydrate, ½ basicity.

Figure 1:
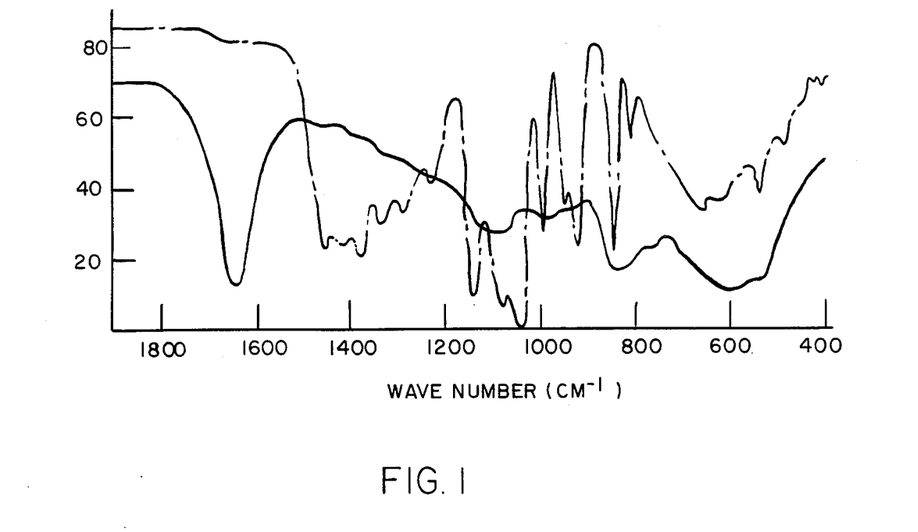
FIG. 1 is a representation of an infra red (IR) spectroscopy scan comparing the curves obtained from scanning unreacted propylene glycol (dotted lines) with sec-propanolato aluminum chlorhydrate (solid line).
Figure 2:
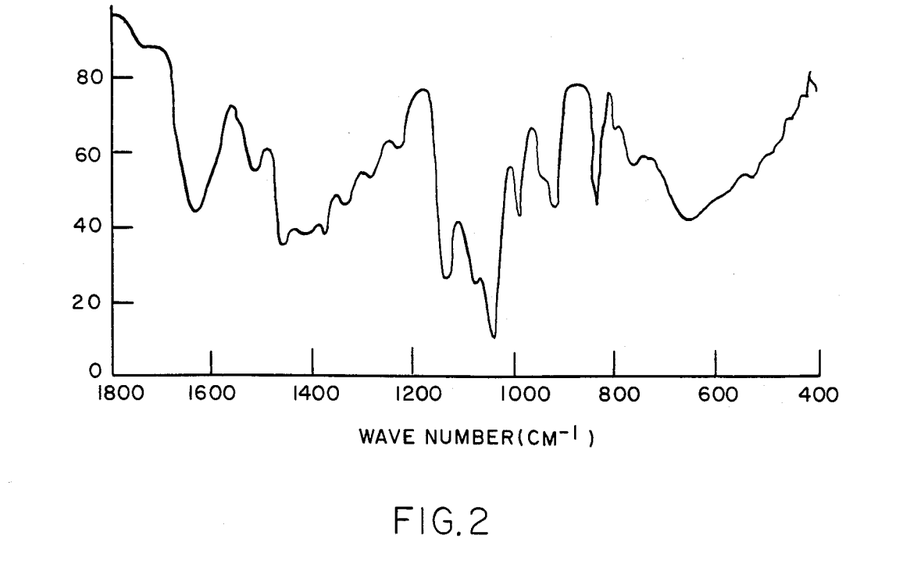
FIG. 2 is the IR scan for the preparation of lysinato functional aluminum zirconium metallo organic complex (see Example 2).
Figure 3:
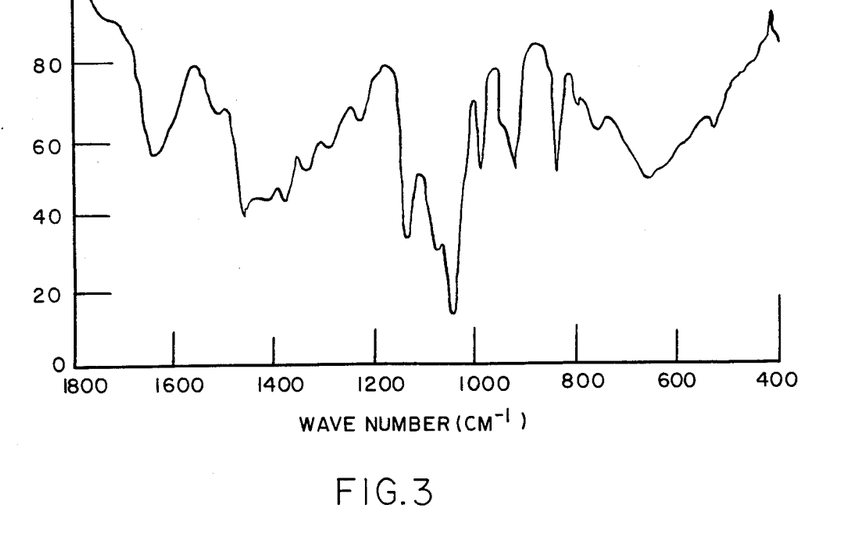
FIG. 3 is the IR scan for the preparation of serinato functional aluminum zirconium metallo organic complex (see Example 3).
Figure 4:
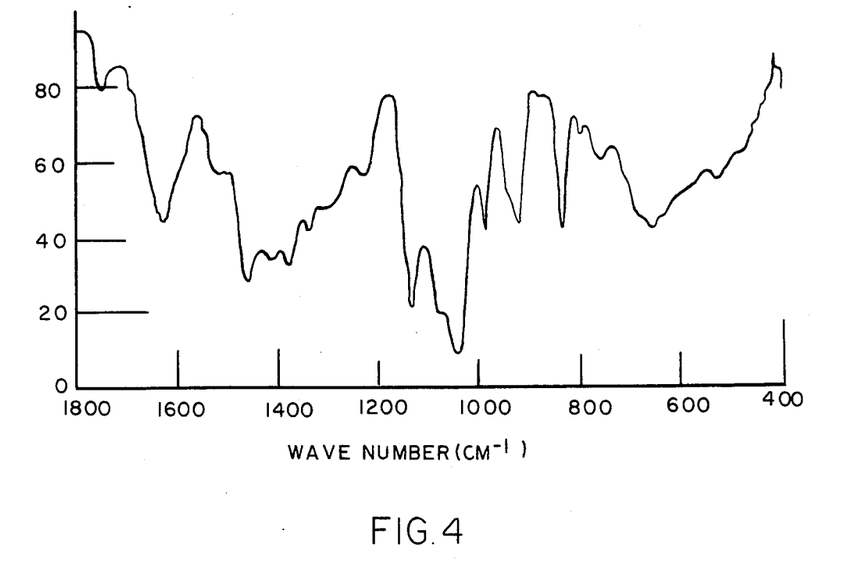
FIG. 4 is the IR scan for the preparation of cysteinato functional aluminum zirconium metallo organic complex (see Example 4).

This is indicated in the IR section shown in FIG. 1. The spectrum of propylene glycol (neat, dotted line in FIG. 1) shows three strong absorbance bands in the 1200-1360 $cm^{-1}$ region at 1230 $cm^{-1}$, 1290 $cm^{-1}$, and 1330 $cm^{-1}$. The latter two bands can be assigned with reasonable certainty to O—H bending vibration modes in the glycol. Upon complexation the O—H bond is destroyed resulting in the disappearance of such bands as clearly revealed in the spectrum of the propanolato aluminum (solid line in FIG. 1). Moreover, the C—O stretching vibrations and related overtone bands found at 840-1230 $cm^{-1}$ have either disappeared or shifted, as seen in the complex spectrum (solid trace).

EXAMPLE 2

Preparation of lysinato functional aluminum zirconium metallo organic complex using zirconium oxychloride solution Zirconium oxychloride solution, 0.0339 moles Zr (20.30 g) is combined with lysine monohydrochloride, 0.119 moles (20.50 g). The mix is agitated and warmed gently (45° C.) to dissolve the lysine monohydrochloride. Propylene glycol, 65.65 g, is then added to the mix and heated at 70° C. for 30 minutes whereupon the mixture becomes clear.

A propylene glycol solution of the product of Example I is prepared by dissolving a 27.92 g portion of sec-propanolato aluminum chlorhydrate, 0.197 moles, in 65.65 g of propylene glycol.

The propylene glycol solution of sec-propanolato aluminum chlorhydrate is then fed for 30 minutes at a temperature of 70° C. to the reactor vessel containing the propylene glycol, lysine hydrochloride, and zirconium oxychloride solution. Heating is maintained at 70° C. for an additional 30 minutes to complete the complexation reaction.

As shown by infrared spectroscopy (FIG. 2), the product thus prepared has the following characteristics: Specific gravity (g/ml)—1.156, Decomposition point (°C.) >300, Flash Point (°F.) >200, Active matter (wt. percent)—25.5, pH (2% solution)—3.6, Aluminum (wt. percent)—2.65, Zirconium (wt. percent)—1.55, Water (wt. percent)—6.8.

Infrared spectroscopy indicates the product thus prepared to be a hybrid complex wherein the carboxy group forms a complex bridge between the aluminum and zirconium centers. An uncomplexed residue comprising 7% of the total lysine monohydrochloride remains, as indicated by the band at 1735 $cm^{-1}$, (—C=O). The complexed material, 93%, is indicated by an intense band at 1635 $cm^{-1}$, representing the weakened (O—C—O—) hybridized bond which results from complexation and concomitant pi bond delocalization over the 3 atom carboxy system (O—C—O). It is noteworthy that formation of the isomeric complex salt would be characterized by a (O—C—O—) absorption band at 1590-1600 $cm^{-1}$. The presence of protonated amino functionality is established by the strong (—N—H) symmetrical bending absorption band at 1515 $cm^{-1}$.

EXAMPLE 3

Preparation of serinato functional aluminum zirconium metallo organic complex using zirconium oxychloride solution Zirconium oxychloride solution, 0.0339 moles Zr (20.30 g) is combined with serine, 0.119 moles (11.79 g). The mix is agitated and warmed gently (45° C.) to dissolve the serine. Propylene glycol, 70.00 g, is then added to the mix and heated at 70° C. for 30 minutes.

A propylene glycol solution of the product of Example 1 is prepared by dissolving a 27.92 g portion of sec-propanolato aluminum chlorohydrate 0.197 moles, in 70.00 g of propylene glycol.

The propylene glycol solution of sec-propanolato aluminum chlorohydrate is then fed for 30 minutes at a temperature of 70° C. to the reactor vessel containing the propylene glycol solution of serine and zirconium oxychloride. Heating is maintained at 70° C. for an additional 30 minutes to complete the complexation reaction. As shown by infrared spectroscopy (FIG. 3) the product thus prepared has the following characteristics: Specific gravity (g/ml) 1.148, Decomposition point (°C.) >300, Flash point (°F.) >200, Active matter (wt. percent)—21.2, pH (2% solution)—3.8, Aluminum (wt. percent)—2.65, Zirconium (wt. percent)—1.55, Water (wt. percent) 6.8.

Infrared spectroscopy indicates the product thus prepared to be a hybrid complex wherein the carboxy group forms a complex bridge between the aluminum and zirconium centers. An uncomplexed residue comprising 2% of the total serine remains as indicated by the band at 1750 cm$^{-1}$ (—C=O). The complexed material, 98%, is indicated by an intense band at 1645 cm$^{-1}$ representing the weakened (O—C—O) hybrid bond which results from complexation and concomitant pi bond delocalization over the 3 atom carboxy system (O—C—O). It is noteworthy that formation of the isomeric complex salt would be characterized by a (O—C—O) absorption band at 1590-1600 cm$^{-1}$. The presence of protonated amino functionality is established by the strong (—N—H) symmetrical bending absorption band at 1515 cm$^{-1}$.

EXAMPLE 4

Preparation of cysteinato functional aluminum zirconium metallo organic complex using zirconium oxychloride solution Zirconium oxychloride solution, 0.0339 moles Zr (20.30 g) is combined with cysteine hydrochloride hydrate, 0.119 moles (19.71 g). The mix is agitated and warmed gently (45° C.) to dissolve the cysteine. Propylene glycol, 66.05 g, is then added to the mix and heated at 70° C. for 30 minutes.

A propylene glycol solution of the product of Example 1 is prepared by dissolving a 27.92 g portion of sec-propanolato aluminum chlorohydrate 0.197 moles, in 66.05 g of propylene glycol.

The propylene glycol solution of sec-propanolato aluminum chlorohydrate is then fed for 30 minutes at a temperature of 70° C. to the reactor vessel containing the propylene glycol solution of cysteine and zirconium oxychloride. Heating is maintained at 70° C. for an additional 30 minutes to complete the complexation reaction as shown by infrared spectroscopy.

The product thus prepared has the following characteristics: Specific gravity (g/ml) 1.169, Decomposition point (°C.) >300, Flash point (°F.) >200, Active matter (wt. percent)—25.2, pH (2% solution)—4.0, Aluminum (wt percent)—2.65, Zirconium (wt. percent)—1.55, Water (wt. percent) 6.8.

Infrared spectroscopy indicates the product thus formed to be a hybrid complex wherein the carboxy group forms a complex bridge between the aluminum and zirconium centers. An uncomplexed residue comprising 21% of the total cysteine remains as indicated by the band at 1750 cm$^{-1}$. The complexed material, 79%, is indicated by an intense band at 1630 cm$^{-1}$ representing the weakened (O—C—O) hybrid bond which results from complexation and concomitant pi bond delocalization over the 3 atom carboxy system (O—C—O). It is noteworthy that formation of the isomeric complex salt would be characterized by an (O—C—O) absorption band at 1590-1600 cm$^{-1}$. The presence of protonated amino functionality is established by the strong (N—H) symmetrical bending absorption band at 1510 cm$^{-1}$.

EXAMPLE 5

Preparation of cysteinato functional aluminum zirconium metallo organic complex using zirconium oxychloride solid A solution of zirconium oxychloride solid, 0.0325 moles Zr (8.35 g) and propylene glycol, 67.00 g, is prepared.

A separate solution of cysteine hydrochloride hydrate, 0.119 moles (19.70 g) in methanol 10.00 g is prepared. The methanolic solution is then added to the zirconium oxychloride propylene glycol solution at 40° C. The mixture is then heated at 70° C. for 30 minutes.

Figure 5:
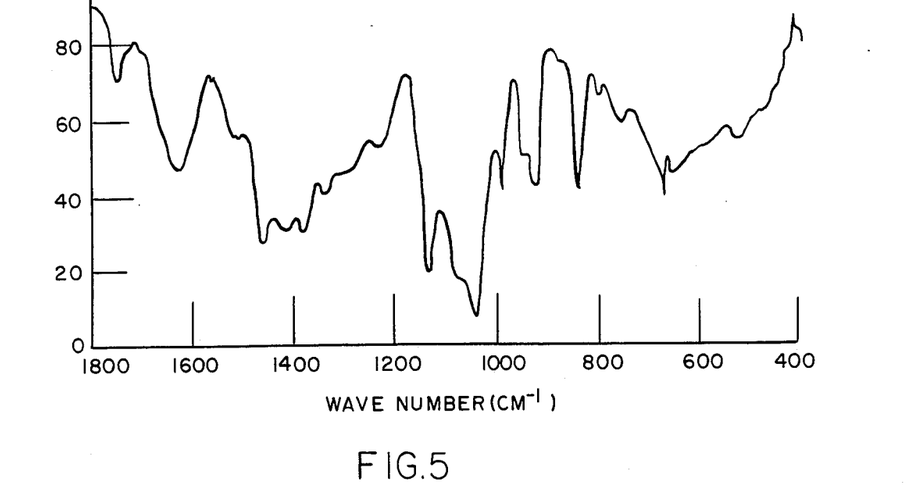
FIG. 5 is the IR scan for the preparation of cysteinato functional aluminum zirconium metallo organic complex (see Example 5).

A propylene glycol solution of the product of Example 1 is prepared by dissolving a 27.92 g portion of sec-propanolato aluminum chlorohydrate in 67.00 g of propylene glycol. The propylene glycol solution of sec-propanolato aluminum chlorohydrate is then fed for 30 minutes at 70° C. to the reactor containing the zirconium oxychloride solid, propylene glycol, methanol and cysteine hydrochloride hydrate. Heating is maintained at 70° C. for an additional 30 minutes to complete the complexation reaction as shown by infrared spectroscopy (FIG. 5).

The product thus prepared has the following characteristics: Specific gravity (g/ml) 1.146, Decomposition point (°C.) >300, Flash point (°F.) >200, Active matter (wt. percent)—25.5, pH (2% solution) 3.9, Aluminum (wt. percent)—2.65, Zirconium (wt. percent)—1.55, Water (wt. percent) <0.5.

Infrared spectroscopy indicates the product thus formed to be a hybrid complex wherein the carboxy group forms a complex bridge between the aluminum and zirconium centers. An uncomplexed residue comprising 15% of the total cysteine remains as indicated by the band at 1750 cm$^{-1}$. The complexed material, 85%, is indicated by an intense band at 1630 cm$^{-1}$ representing the weakened (O—C—O) hybrid bond which results from complexation and concomitant pi bond delocalization over the 3 atom carboxy system (O—C—O). It is noteworthy that formation of the isomeric complex salt would be characterized by a (O—C—O) absorption band at 1590-1600 cm$^{-1}$. The presence of amino functionality is established by the strong (N—H) symmetrical bending absorption band at 1510 cm$^{-1}$.

EXAMPLE 6

Preparation of lysinato functional aluminum zirconium metallo organic complex using zirconium oxychloride solid A solution of zirconium oxychloride solid, 0.0325 moles Zr (8.35 g), propylene glycol, 68.61 g, and water, 6.00 g, is prepared. The mix is heated to 45° C. whereupon lysine monohydrochloride, 20.50 g (0.119 moles) is added. The mix is then heated at 70° C. for 30 minutes.

Figure 6:
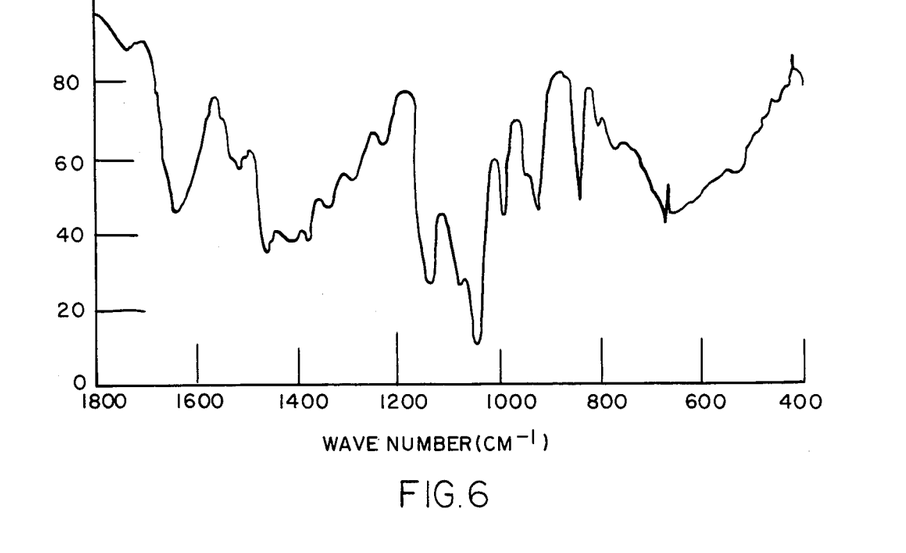
FIG. 6 is the IR scan for the preparation of lysinato functional aluminum zirconium metallo organic complex (see Example 6).

A propylene glycol solution of the product of Example 1 is prepared by dissolving a 27.92 g portion of sec-propanolato aluminum chlorohydrate in 68.61 g of propylene glycol. The propylene glycol solution of sec-propanolato aluminum chlorohydrate is then fed for 30 minutes at 70° C. to the reactor containing zirconium oxychloride solid, propylene glycol, water and lysine monohydrochloride. Heating is maintained at 70° C. for an additional 30 minutes to complete the complexation reaction as shown by infrared spectroscopy (FIG. 6).

The product thus prepared has the following characteristics: Specific gravity (g/ml)—1.151, Decomposition point (°C.) 300, Flash point (°F.) >200, Active matter (wt. percent)—25.9, pH (2% solution)—3.3, Aluminum (wt. percent)—2.65, Zirconium (wt. percent)—1.55, Water (wt. percent)—3.0.

Infrared spectroscopy indicates the product thus formed to be a hybrid complex wherein the carboxy group forms a complex bridge between the aluminum and zirconium centers. An uncomplexed residue comprising <2% of the total lysine remains as indicated by the band at 1740 cm$^{-1}$. The complexed material, >98% is indicated by an intense band at 1640 cm$^{-1}$ representing the weakened (O—C—O) hybrid bond which results from complexation and concomitant pi bond delocalization over the 3 atom carboxy system (O—C—O). It is noteworthy that formation of the isomeric complex salt would be characterized by a (O—C—O) absorption band at 1590-1600 cm$^{-1}$. The presence of amino functionality is established by the strong (N—H) symmetrical bending absorption band at 1515 cm$^{-1}$.

EXAMPLES 7-37

In a manner similar to that detailed for Examples 1 through 6, other amino multifunctional aluminum zirconium metallo organic complex agents were prepared having the substitutents and ratio of substitutents indicated in Table I below.

All of the compositions provide aluminum zirconium metallo organic adhesion promoters which are useful in enhancing adhesion of adhesives, sealants, and coatings to metals and other substrates. It is also possible to obtain useful compositions using other organic reactants and other Al:Zr ratios and basicities, outside the range indicated in Table I, but such products should be checked for stability and effectiveness before use. Preferably, the compositions made in accordance with the present invention have a shelf life of at least about 30 days.

TABLE I

| Example | NH$_2$R$_2$(Y')—COOH | X:Z | (Y:2X + Z) | ZIRCONIUM OXYCHLORIDE SOLID, LIQUID | COSOLVENT | APPEARANCE |
|---|---|---|---|---|---|---|
| 7 | Serine | 1.5:1 | 0.25 | Liquid | None | Clear, colorless |
| 8 | " | | 0.50 | " | " | Clear, colorless |
| 9 | " | | 1.0 | " | " | Precipitate |
| 10 | " | 3:1 | 0.25 | " | " | Clear, colorless |
| 11 | " | | 0.60 | " | " | Clear, colorless |
| 12 | " | | 1.00 | " | " | " |
| 13 | " | 4.5:1 | 0.25 | " | " | " |
| 14 | " | | 0.50 | " | " | " |
| 15 | " | | 1.00 | " | " | Crystal, precipitate |
| 16 | Lysine | 1.5 | 0.50 | " | " | Clear, colorless |
| 17 | " | 3.0:1 | 0.25 | " | " | Clear, colorless |
| 18 | " | | 0.60 | " | " | " |
| 19 | " | | 1.0 | " | " | Precipitate |
| 20 | " | 4.5:1 | 0.50 | " | " | Clear, colorless |
| 21 | Cysteine | 1.5:1 | 0.25 | " | " | " |
| 22 | " | | 0.50 | " | " | " |
| 23 | " | 1.00 | | " | " | " |
| 24 | " | 3.0:1 | 0.25 | " | " | " |
| 25 | " | | 0.50 | " | " | " |
| 26 | " | | 0.60 | " | " | " |
| 27 | " | | 1.00 | " | " | " |
| 28 | " | 4.5:1 | 0.25 | " | " | " |
| 29 | " | | 0.50 | " | " | " |
| 30 | " | | 1.00 | " | " | " |
| 31 | Aspartic | 3:1 | 0.50 | " | " | Precipitate, sl. hazy, two layers |
| 32 | Serine | 3:1 | 0.50:1 | Solid | Water, 2.25% | Cloudy, mod yellow mod precipitate |
| 33 | " | 3:1 | 0.50:1 | " | Water, 3.0% | Sl. hazy, mod yellow no precipitate |
| 34 | " | 3:1 | 0.50:1 | " | Methanol 5% | Cloudy, some precipitate |
| 35 | Lysine | 3:1 | 0.50:1 | " | Water 2.25% | V. cloudy, heavy precipitate mod yellow |
| 36 | " | 3:1 | 0.50:1 | " | Methanol 5.00% | Cloudy, some precipitate |
| 37 | Cysteine | 3:1 | 0.50:1 | " | Water, 2.25% | Hazy, colorless v. sl. precipitate |

EXAMPLE 38

The use of multifunctional amino zirconium aluminum metallo organic adhesion promoters for enhanced adhesion between EPDM adherends A base adhesive comprised of (styrene/butadiene block copolymer) KRATON® rubber (Shell Chemical), various low molecular weight liquid resins, and toluene is prepared having 50 wt. percent solids. A multifunctional amino zirconium metallo organic complex, lysinato (Example 2) or cysteinato (Example 4) is added (0.9 g) to 100 g of the adhesive composition and mixed.

The modified adhesive is then brush applied (15–20 mil) to toluene washed strips of EPDM single-ply roof membrane measuring 1"×6". After air drying for fifteen minutes to a tacky consistency, the strip is folded back upon itself, the two adherends are then gently clamped, and the unit is allowed to fully dry over a period of 2 weeks.

Similarly, EPDM bonded strips are prepared wherein a diamino functional silane (Dow Corning Z-6020) is added (1.25 g) to the 100 g of the same base adhesive composition. The silane containing adhesive is then applied as already described.

The bonded strips are then evaluated for T-peel strength using ASTM D-1876 at a reduced cross head speed of two inches/minute. For each adhesive modification five individual test specimens were evaluated. Table II shows (that whereas the base adhesive provided T-peel strength of only 2-4 pli) the composition of Example 2 (lysinato functional) was responsible for a T-peel strength of 16.5 pli, the composition of Example 4, T-peel strength of 21.2 pli, and the diamino silane, 13.9 pli. All three adhesion promoters enhanced the T-peel strength in excess of 400%; however, when compared to the commercially available amino silane, the composition of Example 2 showed an improvement of 18.7%, and the composition of Example 4 showed an improvement of 45.3%.

TABLE II

| ADHESION PROMOTER | EXAMPLE REFERENCE | T-PEEL STRENGTH, n = 5 pli |
|---|---|---|
| Control | — | 3.0 |
| Diamino silane | — | 13.9 |
| Lysinato | 2 | 16.5 |
| Cysteinato | 4 | 21.2 |

What is claimed is:

1. A composition of matter comprising the reaction product of a chelated aluminum moiety, an organofunctional ligand, and a zirconium oxyhalide, the organofunctional ligand being complexed with and chemically bound to the chelated aluminum moiety and the zirconium moiety, the aluminum moiety having the formula:

$$Al_2(OR_1O)_a A_b B_c$$

wherein A and B are selected from the group consisting of hydroxy and halogen and a, b, and c are numerical values such that $2a+b+c=6$, and $(OR_1O)$ is an alpha, beta or alpha, gamma glycol group in which $R_1$ is an alkyl group having from 1 to 6 carbon atoms;

and wherein the organofunctional ligand is a multifunctional amino acid residue having the formula:

wherein $R_2$ is (1) an alkyl, aryl, or aralkyl group having from 1 to 8 carbon atoms, or (2) a bicyclic N-heterocyclic aryl group having from 7 to 11 carbon atoms; Y' is an amino, hydroxy, carboxy, mercapto, methylmercapto, or sulfide group, and wherein the amine group(s) may be bound to primary or secondary carbon atoms;

and wherein the zirconium oxyhalide moiety which may be used as either an aqueous solution or dry powder has the formula:

$$ZrA_d B_e$$

wherein A, B are as above defined and d and e are numerical values such that $d+e=4$; the molar ratio of chelated aluminum moiety to zirconium oxyhalide moiety being from about 1.5 to 10.0, and the molar ratio of organofunctional ligand to metal being from about 0.05 to 2;

said composition being prepared in a solvent which chelates with the metals, substantially preventing the polymerization thereof.

2. The composition of claim 1, wherein said composition is soluble in mineral spirits, toluene, xylene, ketones, alcohols, glycols, glycol ethers, tetrahydrofuran, oils, dimethylformamide, dimethylsulfone, halogenated hydrocarbons, and water.

3. The composition of matter of claim 1 wherein $R_1$ is an alkyl group of 2 or 3 carbon atoms.

4. The composition of claim 1 wherein the reaction product corresponds to the empirical formula:

$$(Al_2(OR_1O)_a A_b B_c)_X [OC[R_2(Y')NH_2]O]_Y (ZrA_d B_e)_Z$$

wherein X, Y, Z are at least 1, $R_2$ is an alkyl, aryl, aralkyl, or bicyclic N-heterocyclic aryl having from 7 to 11 carbon atoms, Y' is an amino, hydroxy, carboxy, mercapto, methyl mercapto, or sulfide group and wherein the amino group(s) may be bound to primary or secondary carbon atoms, and the ratio of X:Z is from about 1.5:1 to 5:1.

5. The composition of claim 4 wherein the ratio of Y:2X+Z is from about 0.1 to about 1.0.

6. The composition of claim 4 wherein X:Z is about 3:1, Y:2X+Z is about 0.5, A is hydroxy, B is chlorine, $R_1$ is n-propyl or isopropyl, $OC[R_2(Y')NH_2]O$ is serine, a is about 1, b is about 3, and c is about 1, and the zirconium oxyhalide is an aqueous solution of zirconium oxychloride.

7. The composition of claim 4 wherein X:Z is about 3:1, Y:2X+Z is about 1.0, A is hydroxy, B is chlorine, $R_1$ has 3 carbon atoms, $OC[R_2(Y')NH_2]O$ is serine, a is about 1, b is about 3, and c is about 1, and the zirconium oxyhalide is an aqueous solution of zirconium oxychloride.

8. The composition of claim 4 wherein X:Z is about 3:1, Y:2X+Z is about 0.5, A is hydroxy, B is chlorine, $R_1$ has three carbon atoms, $OC[R_2(Y')NH_2]O$ is lysine, a is about 1, b is about 3, and c is about 1, and the zirconium oxyhalide is an aqueous solution of zirconium oxychloride.

9. The composition of claim 4 wherein X:Z is about 3:1, Y:2X+Z is about 0.5, A is hydroxy, B is chlorine, $R_1$ has three carbon atoms, $OC[R_2(Y')NH_2]O$ is cysteine, a is about 1, b is about 3, and c is about 1, and the zirconium oxyhalide is an aqueous solution of zirconium oxychloride.

10. The composition of claim 4 wherein X:Z is about 3:1, Y:2X+Z is about 0.5, A is hydroxy, B is chlorine, $R_1$ has three carbon atoms, $OC[R_2(Y')NH_2]O$ is lysine, a is about 1, b is about 3, and c is about 1, and the zirconium oxyhalide is a zirconium oxychloride powder.

11. The composition of claim 4 wherein X:Z is about 3:1, Y:2X+Z is about 0.5, A is hydroxy, B is chlorine, $R_1$ has three carbon atoms, $OC[R_2(Y')NH_2]O$ is cysteine, a is about 1, b is about 3, and c is about 1, and the zirconium oxyhalide is zirconium oxychloride powder.

12. A method of preparing the composition of matter of claim 1 comprising reacting a chelated aluminum moiety, an organofunctional ligand, and a zirconium oxyhalide, the reaction being carried out in a solvent comprising from about 85 to 94 weight% alkyl glycol having from 1 to 3 carbon atoms, and from about 6 to 15 weight% water, the organofunctional ligand being complexed with and chemically bound to the chelated aluminum moiety and the zirconium moiety, the aluminum moiety having the formula:

$$Al_2(OR_1O)_a A_b B_c$$

wherein A and B are selected from the group consisting of hydroxy and halogen and a, b, and c are numerical values such that $2a+b+c=6$, and $(OR_1O)$ is an alpha, beta or alpha, gamma glycol group in which $R_1$ is an alkyl group having 1 to 6 carbon atoms; the organofunctional ligand is a multifunctional amino acid residue having the formula:

$$\begin{array}{c} Y' \quad O \\ | \quad \| \\ H_2N-R_2-C-O \end{array}$$

wherein $R_2$ is (1) an alkyl, aryl, or aralkyl group having from 1 to 8 carbon atoms, or (2) a bicyclic N-heterocyclic aryl group having from 7 to 11 carbon atoms; Y is an amino, hydroxy, carboxy, mercapto, methylmercapto, or sulfide group, and wherein the amine group(s) may be bound to primary or secondary carbon atoms, and the zirconium oxyhalide moiety is an aqueous solution having the formula:

$$ZrA_d B_e$$

wherein A, B are as above defined and d and e are numerical values such that $d+e=4$; the molar ratio of chelated aluminum moiety to zirconium oxyhalide moiety being from about 1.5 to 10.0, and the molar ratio of organofunctional ligand to metal being from about 0.05 to 2.

13. The method of claim 12 wherein the zirconium oxyhalide is a powder having the formula:

$$ZrA_d B_e$$

wherein A, B are as above defined and d and e are numerical values such that $d+e=4$, the molar ratio of chelated aluminum moiety to zirconium oxyhalide moiety being from about 1.5 to 10.0, and the molar ratio of organofunctional ligand to metal being from about 0.05 to 2, the reaction being carried out in a solvent comprising 94-98 weight% glycol having 1-3 carbon atoms, and 2 to 6 weight% of either water or lower alcohol having 1 to 3 carbon atoms.

14. The method of claim 12, wherein the reaction product corresponds to the empirical formula:

$$(Al_2(OR_1O)_a A_b B_c)_X [OC(R_2(Y')NH_2)O]_Y (ZrA_d B_e)_Z$$

wherein X, Y, Z are at least 1, $R_1$ is an alkyl of 2-3 atoms, and $OC[R_2(Y')NH_2]O$ is amino acid wherein $R_2$ is (1) an alkyl, aryl, or aralkyl group having from 1 to 8 carbon atoms, or (2) a bicyclic N-heterocyclic aryl group having from 7 to 11 carbon atoms; Y is an amino, hydroxy, carboxy, mercapto, methylmercapto, or sulfide group, and wherein the amine group(s) may be bound to primary or secondary carbon atoms.

15. The method of claim 13, wherein the reaction product corresponds to the empirical formula:

$$(Al_2(OR_1O)_a A_b B_c)_X [OC(R_2(Y')NH_2)O]_Y (ZrA_d B_e)_Z$$

wherein X, Y, Z are at least 1, $R_1$ is an alkyl of 2-3 atoms, and $OC[R_2(Y')NH_2]O$ is amino acid wherein $R_2$ is (1) an alkyl, aryl or aralkyl group having from 1 to 8 carbon atoms; or (2) a bicyclic N-heterocyclic aryl group having from 7 to 11 carbon atoms; Y is an amino, hydroxy, carboxy, mercapto, methylmercapto, or sulfide group, and wherein the amine group(s) may be bound to primary or secondary carbon atoms.

16. The method of claim 12 wherein the ratio of Y:2X+Z is from about 0.1 to about 1.0, and $R_1$ is an alkyl group of 2 or 3 carbon atoms, and $OC[R_2(Y')NH_2]O$ is serine, lysine, or cysteine.

17. The method of claim 13 wherein the ratio of Y:2X+Z is from about 0.1 to 1.0 and $R_1$ is an alkyl group of 2 or 3 carbon atoms, and $OC(R_2(Y')NH_2)O$ is serine, lysine, or cysteine.

18. The method of claim 12 further comprising forming the chelated aluminum moiety by reacting an aluminum halohydrate with a bidentate chelating agent having the formula $HOR_1OH$ wherein $R_1$ is an alkyl group having 1 to 6 carbon atoms.

19. The method of claim 13 further comprising forming the chelated aluminum moiety by reacting an aluminum halohydrate with a bidentate chelating agent having the formula $HOR_1OH$ wherein $R_1$ is an alkyl group having 1 to 6 carbon atoms.

20. The method of claim 18 wherein the chelated aluminum moiety, the organofunctional ligand and zirconium oxyhalide are reacted in a solvent which is from about 85 to 94 weight% alkyl glycol having from 1 to 3 carbon atoms, and from about 6 to 15 weight% water, the final concentration of adhesion promoter in the solvent being from about 15 to 60 percent.

21. The method of claim 19 wherein the chelated aluminum moiety, the organofunctional ligand and zirconium oxyhalide are reacted in a solvent which is from about 94 to 98 weight% alkyl glycol having from 1 to 3 carbon atoms, and from about 2 to 6 weight% of either water or lower alcohol having from 1 to 3 carbon atoms.

* * * * *